(12) United States Patent
Chang et al.

(10) Patent No.: US 11,389,412 B2
(45) Date of Patent: Jul. 19, 2022

(54) CURCUMINOID CHLOROPHYLLIN (CHL) COMPOSITIONS AND METHODS OF PREPARATION AND USE

(71) Applicant: InovoBiologic Inc., Calgary (CA)

(72) Inventors: Chuck Chang, Burnaby (CA); Sangho Lee, Burnaby (CA); Youngse Jang, Burnaby (CA); Yoon Seok Roh, Burnaby (CA)

(73) Assignee: InovoBiologic Inc., Calgary (CA)

( * ) Notice: Subject to any disclaimer, the term of this patent is extended or adjusted under 35 U.S.C. 154(b) by 0 days.

(21) Appl. No.: 16/143,188

(22) Filed: Sep. 26, 2018

(65) Prior Publication Data

US 2019/0105285 A1    Apr. 11, 2019

Related U.S. Application Data

(60) Provisional application No. 62/564,819, filed on Sep. 28, 2017.

(51) Int. Cl.
*A61K 31/12* (2006.01)
*A61K 9/48* (2006.01)

(52) U.S. Cl.
CPC ............ *A61K 31/12* (2013.01); *A61K 9/4858* (2013.01); *A61K 9/4866* (2013.01); *A61K 9/4875* (2013.01)

(58) Field of Classification Search
CPC .... A61K 31/12; A61K 9/4866; A61K 9/4858; A61K 9/4875
See application file for complete search history.

(56) References Cited

U.S. PATENT DOCUMENTS

| | | | |
|---|---|---|---|
| 7,883,728 B2 | 2/2011 | Antony | |
| 8,187,615 B2 | 5/2012 | Friedman | |
| 8,551,507 B2 | 10/2013 | Liu | |
| 2006/0189543 A1* | 8/2006 | Rosenbloom | A61K 31/07 424/94.4 |
| 2010/0316631 A1 | 12/2010 | Safavy | |
| 2011/0033525 A1 | 2/2011 | Liu | |
| 2013/0274343 A1 | 10/2013 | Deshpande et al. | |
| 2015/0132443 A1* | 5/2015 | Bhakta | A23L 33/30 426/87 |

FOREIGN PATENT DOCUMENTS

| | | |
|---|---|---|
| WO | 2012024405 | 2/2012 |
| WO | 2013175507 | 11/2013 |
| WO | 2014025672 | 2/2014 |
| WO | 2014068597 | 5/2014 |
| WO | 2015025263 | 2/2015 |

\* cited by examiner

*Primary Examiner* — Hong Yu
(74) *Attorney, Agent, or Firm* — Christensen O'Connor Johnson Kindness PLLC

(57) ABSTRACT

Provided herein are solid form water soluble curcuminoid compositions, including a curcuminoid; and a solubilization matrix, wherein the solubilization matrix is selected from one or more of the following: (i) chlorophyllin (CHL); (ii) green tea extract; (iii) epigallocatechin gallate (EGCG); (iv) Rutin; and (v) an aromatic amino acid. Alternatively, the solubilization matrix may include methylsulfonylmethane (MSM). Also provided herein are methods for producing curcuminoid compositions.

8 Claims, 6 Drawing Sheets

CURCUMINOID CHLOROPHYLLIN (CHL) COMPOSITIONS AND METHODS OF PREPARATION AND USE

TECHNICAL FIELD

This invention relates to the field of curcuminoids. In particular, the invention relates to water soluble curcuminoid compositions and methods for preparing water-soluble curcuminoid compositions.

BACKGROUND

Curcumin is the major curcuminoid of the Indian curry spice turmeric. Curcuminoids provide the major yellow color pigment of turmeric, which is derived from the rhizome of the *Curcuma longa linn* plant and it has been traditionally used in the treatment of skin wounds, inflammation, tumors et al.

Although raw turmeric contains more than 100 components, its characteristic yellow color is derived from various curcuminoids. Curcuminoids have a chemical structure consisting of 2 aromatic rings joined by a 7-carbon chain with various substituents.

Curcumin (1,7bis (4-hydroxy-3-methoxy phenyl)-1,6 heptadiene-3,5-dione) is a hydrophobic polyphenol derivative which is a potent antioxidant derived from the spice turmeric. Commercial "curcumin" is a mixture of diarylheptanoid compounds, that usually a combination of about 77% diferuloylmethane (i.e. curcumin), 17% demethoxycurcumin, and 6% of bisdemethoxycurcumin.

Curcuminoids are the primary active ingredients of *Cucuma longa* rhizome (the turmeric plant). These curcuminoids are often identified as curcumin 1 (diferuylmethane), curcumin 2 (demethoxycurcumin), curcumin 3 (didemethoxycurcumin) and cyclocurcumin (A. Goel and A. B. Kunnumakkara, 2008). Curcumin 1 (diferuylmethane) is the most potent of the naturally occurring curcuminoids.

Curcuminoids are natural phenolic compounds that are responsible for the yellow color of turmeric. Curcumin exists in several tautomeric forms.

Curcuminoids are generally hydrophobic compounds thought to have a variety of therapeutic benefits (for example, anti-inflammatory, anti-oxidant, anti-cancerous activities). However, their therapeutic use has been limited by their hydrophobicity which results in poor solubility and rapid elimination from the body (i.e. low bioavailability).

While the poor bioavailability of curcumin is attributable to its poor absorption in the body, it is also quickly metabolized and rapidly eliminated from the body.

Curcuminoids have been shown to have potent activity against pancreatic cancer, to inhibit gastrointestinal carcinogenesis, and to protect against oxidative stress. It is also reported to have chemopreventative, chemotherapeutic, chemosensitizing, and radio-protective in normal cells and radiosensitizing in cancer cells. Curcumin has been reported to exhibit anti-tumor and anti-apoptotic properties and to suppress the growth of a variety of cancer cell lines in the laboratory and prevent the appearance of cancers in animal studies (Araujo and Leon, 2001).

In order to overcome the poor bioavailability of curcuminoid compounds, various efforts have been made to increase their bioavailability through complexing with cyclodextrins, micelles and nanoparticles.

Curcumin has chemo preventive, anti-neoplastic and anti-inflammatory properties in preclinical animal models (Gary J. Kelloff New Agents for Cancer Chemoprevention *Journal of Cell Biochemistry* (1996) 63 Supplement S26:1-28).

S. K Kulkarni demonstrate a role for curcumin in enhancing neurogenesis, notably in the frontal cortex and hippocampal regions of the brain ("Potentials of Curcumin as an Antidepressant" *Scientific World Journal* (2009) 9:1233-1241).

The synthesis and physiochemical characterization of a polymer based nanoparticle of curcumin called 'nanocurcumin' with less than 100 nm particle size was described by Savita Bisht et al. ("Polymeric nanoparticle-encapsulated curcumin ("nanocurcumin"): a novel strategy for human cancer therapy Journal of Nanobiotechnology (2007)5:3). The nanocurcumin was found to have similar in vitro activity as that of free curcumin in pancreatic cell lines.

WO2013175507 titled "Novel highly bioavailable, water soluble and sustained release nano-formulations of hydrophobic plant derived compounds and extracts" describes a nano-emulsified composition to enhance bioavailability of curcuminoids. The concentration of the emulsifier phase in the nanoformulations ranges from 60% to 95%. In addition, the application describes the use of emulsifiers which are anionic, cationic or non-ionic selected from but not limited to Polysorbates preferably Polysorbate 80 and Polysorbate 20, Polyethylene glycols preferably Polyethylene glycol 200 and Polyethylene glycol 400, Polyethylene glycol esters and Glycerol esters and also tabulates a series of composition of nanoformulations using hydrophobic compounds and also disclosed a process of pre-heating the emulsifier phase to a temperature below the melting point of the hydrophobic active ingredient. Analytical results for the particle size of CurQlife (curcumin), morphological characteristics of CurQlife are provided, along with an aqueous phase curcumin concentration ranging from 5 to 20%. Furthermore, the maximum curcumin concentration achieved in human pharmacokinetic study was about 25 ng/mL.

U.S. Pat. No. 7,883,728 titled "Composition to enhance the bioavailability of curcumin" provides a method to improve bioavailability of curcumin preparation of a composition containing purified curcuminoid and purified oil and discloses a methodology to prepare a composition for enhanced bioavailability. The composition comprises a curcuminoid mixture consisting of demethoxycurcumin and bisdemethoxycurcumin and the essential oil arturmerone. The percent ratios of the composition consist of a range of 24% to 96% of curcuminoids combined with a range of 4% to 50% of the essential oil. The bioavailability of curcumin in human was shown to reach a maximum of about 93 ng/g.

WO2012024405 titled "Curcumin compositions and uses thereof" describes a composition and a method of increasing the bioavailability of curcumin. The composition is suitable for modifying DNA methylation and for treatment of cancer. The composition comprises curcumin and excipient polymers like polyethoxylated castor oil, polyoxyethylenesorbitan ester and polyethylene glycol. The application described the increased bioavailability of curcumin by using gel formulation and the formulation is safe, tolerated and effective in treatment of leukemia and breast cancer. The plasma level of curcumin was high in human volunteers thus increasing the bioavailability of curcumin. However, the invention is silent with respect to the absorption of curcumin from blood and its dispersibility, which affects the bioavailability.

WO2014068597, titled "Formulation of curcumin with enhanced bioavailability of curcumin and method of preparation and treatment thereof", provides a medicinal composition useful for the treatment of head and neck cancer premalignant lesions comprising (a) curcuminoid mixture and (b) an essential oil of turmeric. The weight ratios of curcuminoid mixtures to turmeric essential oil ranging from about 1:3 to about 99:1. Also disclosed, is a method of treating head and neck oral premalignant lesion by the administration of medicinal composition comprising curcuminoid mixture and added essential oil of turmeric to patients suffering from such disease.

WO2015025263 titled "A novel composition of curcumin with enhanced bioavailability", discloses a curcumin composition for increasing the bioavailability of curcumin, which consists of curcumin mixture and a water extract of turmeric in a ratio of 70:30, wherein the curcumin mixture comprises curcumin dry crystals, volatile oil, fixed oil and the water extract comprises soluble proteins, dietary fibers and carbohydrates extracted from turmeric, and the composition also consists of a natural emulsifier isolated from *Quillaja saponaria* and lecithin and a method of preparing the composition.

US patent publication US2010/031663 titled "Water Soluble Curcumin-based Compositions" discloses the design and synthesis of water soluble curcumin-based compositions, methods for synthesizing the compositions and methods of treatment using the compositions.

US patent publication US2013/0274343 titled "Water Soluble Composition comprising Curcumin having enhanced bioavailability and process thereof" describes a water soluble composition having enhanced bioavailability and a process for its preparation.

U.S. Pat. No. 8,551,507, titled "Terpene glycosides and their combinations as solubilizing agents" discloses methods and compositions for enhancing solubility of organic compounds including curcuminoids with terpene glycosides, wherein combinations include curcuminoids with 1% to 40% w/v mogroside V and curcuminoids with 1% to 40% w/v geniposide. Stevioside was shown to enhance the solubility of clofazinine, digoxin, oleandrin, nifedipine, and amiodarone, but does not appear to have been combined with curcumin.

US patent publication US2011/0033525, titled "Diterpene Glycosides as Natural Solubilizers" discloses methods for enhancing curcuminoid solubility by mixing it with water and a diterpene glycoside such as rubusoside, rebaudioside, steviol monoside and stevioside. Rubusoside was shown to increase the solubility of curcumin in water by a factor of 285 and another example discloses that 5% stevioside in water was equally effective to rubusoside in solubilizing curcumin. All of the compositions disclosed as enhancing solubility were aqueous solutions and no solid form composition was disclosed.

PCT/US2013/053585 describes water soluble compositions of curcumin were formulated containing macrogolglycerol hydroxystearate (polyoxyl 40 castor oil) and curcumin extract that is 99% purel, 1,7-Bis(4-hydroxy-3-methoxyphenyl)-1,6-heptadiene-3,5-dione by HPLC, wherein the polyoxyl 40 castor oil (non-ionic surfactant) was heated and stirred to a temperature of about 125° F. (about 52° C.), and the curcumin powder was slowly mixed with the polyoxyl castor oil until a clear viscous solution was formed containing dissolved curcumin powder. The curcumin emulsion was then slowly added to warm water (100-125° F.) until a crystal clear solution was formed.

U.S. Pat. No. 8,187,615 discloses non-aqueous compositions for oral delivery of insoluble bioactive agents (for example, curcumin) wherein polyethylene glycol is one of the pharmaceutically acceptable water-miscible non-aqueous solvents.

SUMMARY

The present invention is based, in part, on the discovery that curcuminoids are made more water soluble and thus more bioavailable to a subject when combined with a solubilization matrix as described herein.

In one aspect, there is provided a method of producing a solid form water soluble curcuminoid composition, the method including: (a) mixing a curcuminoid and a solubilization matrix to form a mixture; (b) adjusting the temperature of the mixture to between about 37° C. and about 190° C. to dissolve the curcuminoid; and (c) cooling the mixture to permit the curcuminoid and the solubilization matrix composition to achieve a solid form; wherein the solubilization matrix is selected from one or more of the following: (i) chlorophyllin (CHL); (ii) green tea extract; (iii) epigallocatechin gallate (EGCG); (iv) Rutin; and (v) an aromatic amino acid.

The solubilization matrix may further include methylsulfonylmethane (MSM). The aromatic amino acids may be tyrosine, tryptophan, or phenylalanine. The mixture may further include an organic solvent. The organic solvent may be selected from: methanol; ethanol; propanol; butanol; acetonitrile; and acetone. The organic solvent may be added: (a) before adjusting the temperature of the mixture in (b); (b) during the adjusting the temperature of the mixture in (b); or (c) the curcumin may be dissolved in the organic solvent before mixing with the solubilization matrix. The temperature of the mixture may be kept between about 60° C. and about 90° C. for 20 to 200 minutes to facilitate organic solvent evaporation. The temperature of the mixture may be kept between about 70° C. and about 90° C. for 20 to 200 minutes to facilitate organic solvent evaporation. The temperature of the mixture may be kept between about 80° C. and about 90° C. for 20 to 200 minutes to facilitate organic solvent evaporation. The temperature of the mixture may be kept between about 60° C. and about 90° C. for 40 to 200 minutes to facilitate organic solvent evaporation. The temperature of the mixture may be kept between about 60° C. and about 90° C. for 50 to 200 minutes to facilitate organic solvent evaporation. The temperature of the mixture may be kept between about 60° C. and about 90° C. for 60 to 200 minutes to facilitate organic solvent evaporation. The temperature of the mixture may be kept between about 60° C. and about 90° C. for 70 to 200 minutes to facilitate organic solvent evaporation. The temperature of the mixture may be kept between about 60° C. and about 90° C. for 80 to 200 minutes to facilitate organic solvent evaporation. The temperature of the mixture may be kept between about 60° C. and about 90° C. for 90 to 200 minutes to facilitate organic solvent evaporation. The temperature of the mixture may be kept between about 60° C. and about 90° C. for 10 to 120 minutes to facilitate organic solvent evaporation.

The curcuminoid component of the solid form water soluble curcuminoid composition may be between about 5% and about 70% by weight. The curcuminoid component of the solid form water soluble curcuminoid composition, may be between about 10% and about 60% by weight. The curcuminoid component of the solid form water soluble curcuminoid composition may be between about 10% and about 50% by weight. The curcuminoid component of the solid form water soluble curcuminoid composition may be between about 10% and about 40% by weight. The curcuminoid component of the solid form water soluble curcuminoid composition may be between about 10% and about 30% by weight. The curcuminoid component of the solid form water soluble curcuminoid composition may be between about 10% and about 20% by weight.

The solid form water soluble curcuminoid composition may be isolated. The curcuminoid component of the solid form water soluble curcuminoid composition may be between about 5% and about 80% by weight. The curcuminoid component of the solid form water soluble curcuminoid composition may be between about 5% and about 90% by weight.

The solubilization matrix component of the solid form water soluble curcuminoid composition, may be between about 30% and about 95% by weight. The solubilization matrix component of the solid form water soluble curcuminoid composition, may be between about 40% and about 80% by weight. The solubilization matrix component of the solid form water soluble curcuminoid composition, may be between about 40% and about 70% by weight. The solubilization matrix component of the solid form water soluble curcuminoid composition, may be between about 40% and about 60% by weight. The solubilization matrix component of the solid form water soluble curcuminoid composition may be between about 50% and about 70% by weight.

The solubilization matrix component of the solid form water soluble curcuminoid composition, may be between about 20% and about 95% by weight. The solubilization matrix component of the solid form water soluble curcuminoid composition, may be between about 10% and about 95% by weight.

One of the solubilization matrix components may be a CHL and the CHL may be between about 30% and about 90% by weight. One of the solubilization matrix components may be a CHL and the CHL may be between about 40% and about 80% by weight. One of the solubilization matrix components may be a CHL and the CHL may be between about 40% and about 70% by weight. One of the solubilization matrix components may be a green tea extract and the green tea extract may be between about 30% and about 90% by weight. One of the solubilization matrix components may be a green tea extract and the green tea extract may be between about 40% and about 80% by weight. One of the solubilization matrix components may be a green tea extract and the green tea extract may be between about 40% and about 70% by weight. One of the solubilization matrix components may be a EGCG and the EGCG may be between about 30% and about 90% by weight. One of the solubilization matrix components may be a EGCG and the EGCG may be between about 40% and about 80% by weight. One of the solubilization matrix components may be a EGCG and the EGCG may be between about 40% and about 70% by weight. The solubilization matrix component may be Rutin and the Rutin may be between about 30% and about 90% by weight. The solubilization matrix component may be Rutin and the Rutin may be between about 40% and about 80% by weight. The solubilization matrix component may be Rutin and the Rutin may be between about 40% and about 70% by weight. The solubilization matrix component may be an aromatic amino acid and the aromatic amino acid may be between about 30% and about 90% by weight. The solubilization matrix component may be an aromatic amino acid and the aromatic amino acid may be between about 40% and about 80% by weight. The solubilization matrix component may be an aromatic amino acid and the aromatic amino acid may be between about 40% and about 70% by weight.

The organic solvent may be between 3 and 90 times the total curcumin mixture by weight. The organic solvent may be between 3 and 80 times the total curcumin mixture by weight. The organic solvent may be between 3 and 70 times the total curcumin mixture by weight. The organic solvent may be between 3 and 60 times the total curcumin mixture by weight. The organic solvent may be between 3 and 50 times the total curcumin mixture by weight. The organic solvent may be between 3 and 40 times the total curcumin mixture by weight. The organic solvent may be between 3 and 30 times the total curcumin mixture by weight. The organic solvent may be between 3 and 20 times the total curcumin mixture by weight. The organic solvent may be between 3 and 10 times the total curcumin mixture by weight. The organic solvent may be between 3 and 9 times the total curcumin mixture by weight. The organic solvent may be between 3 and 8 times the total curcumin mixture by weight. The organic solvent may be between 3 and 7 times the total curcumin mixture by weight. The organic solvent may be between 3 and 6 times the total curcumin mixture by weight. The organic solvent may be between 3 and 5 times the total curcumin mixture by weight. The organic solvent may be between 3 and 4 times the total curcumin mixture by weight. The organic solvent may be 3 times the total curcumin mixture by weight.

The organic solvent may be ethanol and the ethanol may be evaporated for about 30 to about 120 minutes. The organic solvent may be ethanol and the ethanol may be evaporated for about 30 to about 110 minutes. The organic solvent may be ethanol and the ethanol may be evaporated for about 30 to about 100 minutes. The organic solvent may be ethanol and the ethanol may be evaporated for about 30 to about 90 minutes. The organic solvent may be ethanol and the ethanol may be evaporated for about 30 to about 80 minutes. The organic solvent may be ethanol and the ethanol may be evaporated for about 30 to about 70 minutes. The organic solvent may be ethanol and the ethanol may be evaporated for about 30 to about 60 minutes. The temperature for evaporation of the ethanol may be between about 60° C. and about 85° C. The temperature for evaporation of the ethanol may be between about 60° C. and about 80° C.

In another embodiment, there may be provided a method of producing a solid form water soluble curcuminoid composition, the method may include: (a) curcuminoid may be dissolved in ethanol to about 20% w/w concentration; (b) CHL may be mixed and heated in a vacuum chamber to at least about 50° C.; (c) the curcumin and ethanol solution may be sprayed into the vacuum chamber slowly; and (d) the contents of the vacuum chamber may be dried under vacuum.

The method may further include encapsulation. The product may be encapsulated with lubricants and fillers.

In a further embodiment, there may be provided a product produced by one of the above methods.

In a further embodiment, there may be provided a composition, the composition including: (a) a curcuminoid; and (b) a solubilizer, wherein the solubilizer may be selected from one or more of: (i) chlorophyllin (CHL); (ii) green tea extract; (iii) epigallocatechin gallate (EGCG); (iv) Rutin; and (v) an aromatic amino acid.

The curcuminoid may be between 10-30% w/w and the solubilizer may be between 70-90% w/w. The weight percentage of curcuminoid may be between about 5% and about 70%. The solubilizer may be chlorophyllin. The chlorophyllin may be sodium magnesium chlorophyllin, sodium zinc chlorophyllin, sodium copper chlorophyllin, chlorophyll paste or oil-soluble chlorophyll.

The weight percentage of solubilizer may be between about 10% and about 50%. The weight percentage of solubilizer may be between about 20% and about 50%. The weight percentage of solubilizer may be between about 30% and about 50%. The weight percentage of solubilizer may be between about 40% and about 50%. The weight percentage of solubilizer may be between about 10% and about 40%. The weight percentage of solubilizer may be between about 10% and about 30%. The weight percentage of solubilizer may be between about 10% and about 20%. The solubilizer may be green tea extract. The solubilizer may be chlorophyllin (CHL). The solubilizer may be epigallocatechin gallate (EGCG). The solubilizer may be rutin. The solubilizer may be an aromatic amino acid. The weight percentage of solubilizer may be between about 10% and about 90%. The weight percentage of solubilizer may be between about 10% and about 80%. The weight percentage of solubilizer may be between about 10% and about 70%. The weight percentage of solubilizer may be between about 10% and about 60%. The weight percentage of solubilizer may be between about 10% and about 50%. The weight percentage of solubilizer may be between about 10% and about 40%. The weight percentage of solubilizer may be between about 10% and about 30%. The weight percentage of solubilizer may be between about 10% and about 20%. The weight percentage of solubilizer may be between about 20% and about 90%. The weight percentage of solubilizer may be between about 30% and about 90%. The weight percentage of solubilizer may be between about 40% and about 90%. The weight percentage of solubilizer may be between about 50% and about 90%. The weight percentage of solubilizer may be between about 60% and about 90%. The weight percentage of solubilizer may be between about 70% and about 90%. The weight percentage of solubilizer may be between about 80% and about 90%.

In a further embodiment, there may be provided a composition, the composition including: (a) a curcuminoid, wherein the curcuminoid may be between 10-30% w/w; and (b) a solubilizer, wherein the solubilizer may be selected from one or more of: (i) chlorophyllin (CHL); (ii) green tea extract; (iii) epigallocatechin gallate (EGCG); (iv) Rutin; and (v) an aromatic amino acid wherein the solubilizer may be between 70-90% w/w.

The composition may be encapsulated. The composition may be encapsulated with pharmaceutically acceptable lubricants and fillers.

DETAILED DESCRIPTION

Figure 1:
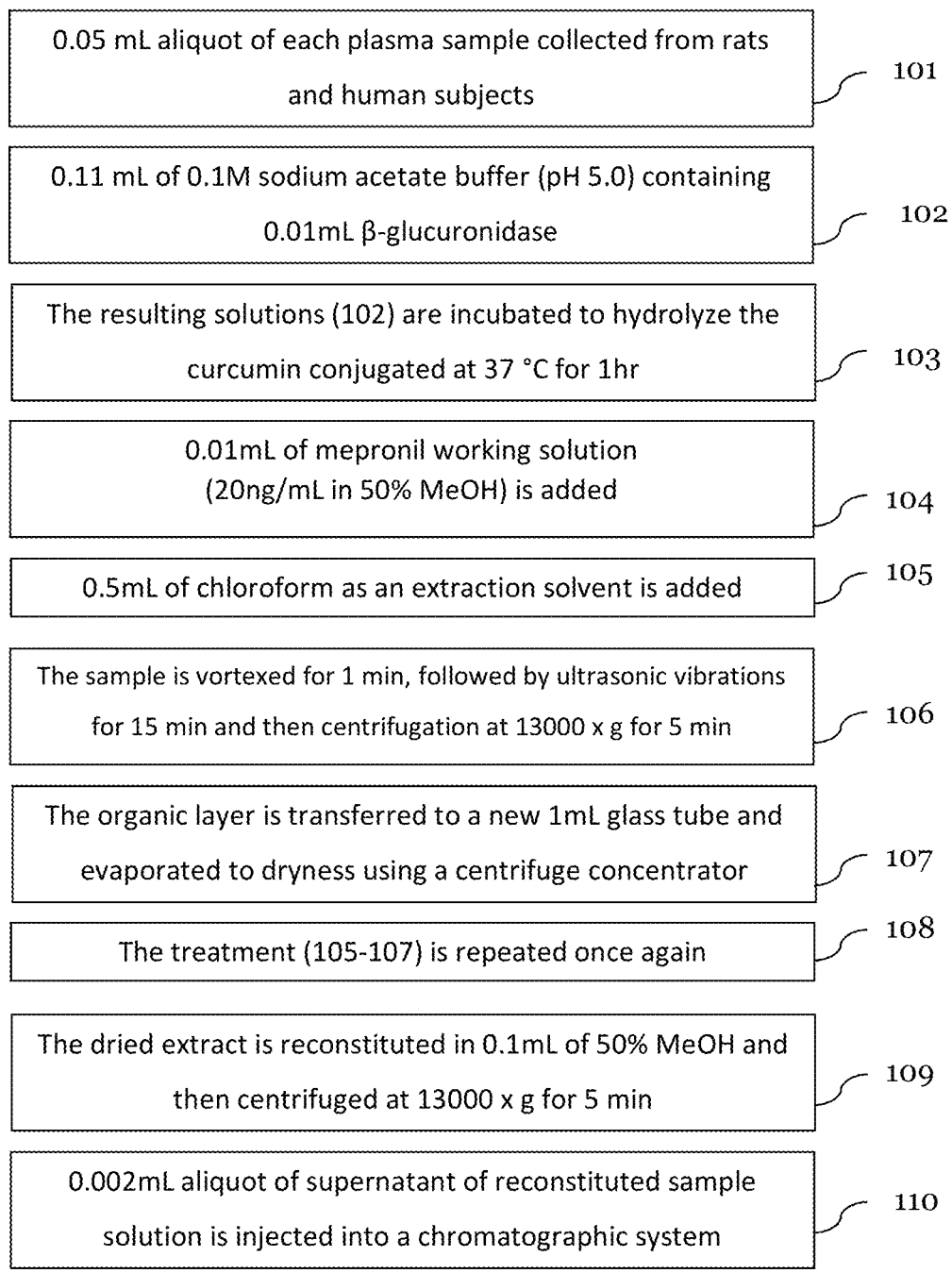
FIG. 1 shows a flow chart of the extracting process for plasma sample.

Any terms not directly defined herein shall be understood to have the meanings commonly associated with them as understood within the art of the invention.

The term "curcuminoid" as used herein, is meant to encompass a variety of linear diarylheptanoid compounds of natural and synthetic origins or even compounds of natural origin that are subsequently synthetically modified. A diarylheptanoid consists of two aromatic rings (aryl groups) joined by a seven carbons chain (heptane) or seven carbons forming a ring and linear linker (for example, see cyclocurcumin) and allowing for various substituents. Common curcuminoids may include one or more of the following:

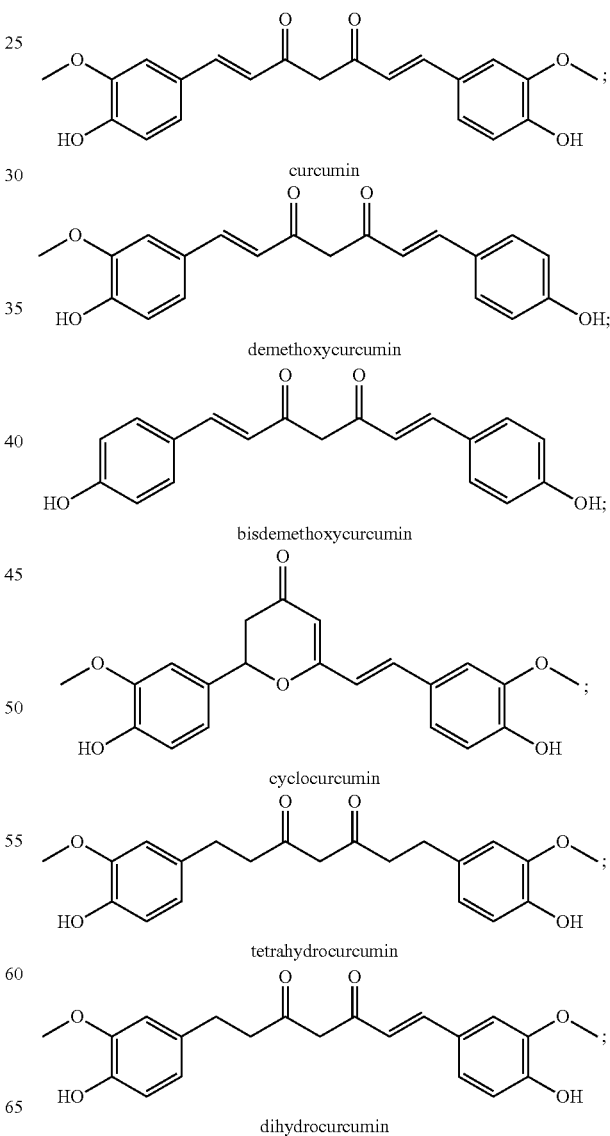

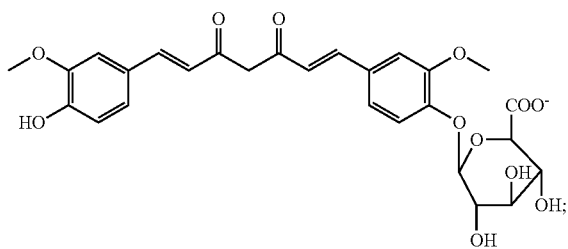

curcumin-glucoronoside

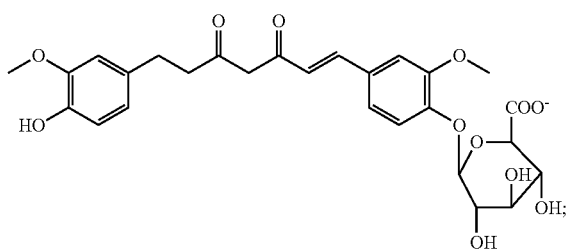

dihydrocurcumin-glucoronoside

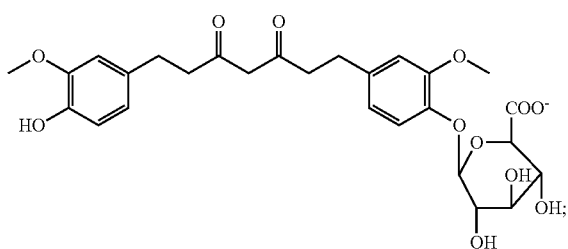

tetrahydrocurcumin-glucoronoside

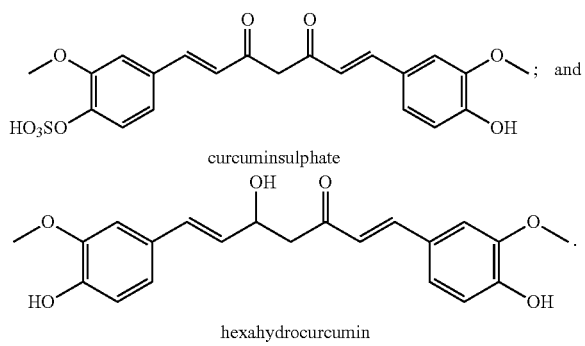

curcuminsulphate hexahydrocurcumin

The Indian spice turmeric, which is derived from the rhizome of the plant *Curcuma longa*, is a natural source of the curcumin. However, curcuminoids are found in many other plant families and the extracted curcuminoids may be modified to form curcuminoids derivatives. The most common curcuminoid derivatives are substituted on the phenyl groups, but may also have variations in the linking chain as shown above.

The term "chlorophyllin" (CHL) as used herein refers to a semi-synthetic food additive derived from chlorophyll, which may be extracted, for example, from alfalfa (*Medicago sativa*) or spinach (*Spinacia oleracea*), using any one or a combination of the solvents acetone, ethanol, and hexane. The particular CHL (i.e. CAS Number: 11006-34-1) is determined by the identity of the cations associated with the anion. The most common form is a sodium/copper CHL derivative. Sodium copper CHL is a green to black powder prepared from chlorophyll by saponification and replacement of magnesium by copper. The structure of sodium copper CHL is:

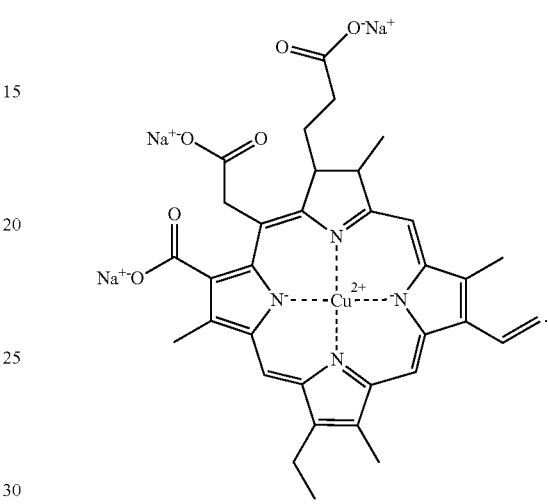

However, the sodium/magnesium CHL derivative is an alternative CHL. Similarly, sodium/zinc CHL derivative, chlorophyll paste or oil-soluble chlorophyll may be selected.

The term "green tea extract" as used herein is meant to encompass a tea extract from *Camellia sinensis*. For example, powdered decaffeinated green tea extract is available in numerous forms and purities from Millipore Sigma™ (i.e. CAS Number: 84650-60-2). The primary ingredient of which is epigallocatechin gallate (EGCG), is most abundant catechin in tea (i.e. for example, CAS Number: 989-51-5), which has the general structure

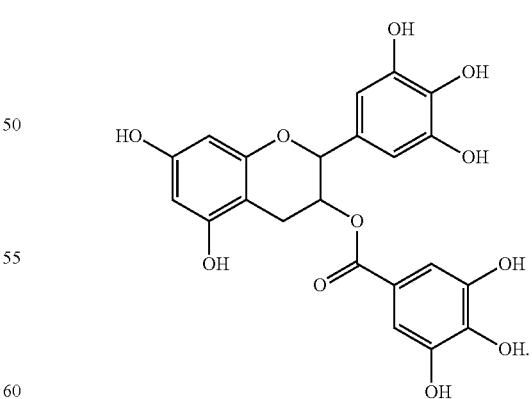

The term "Rutin" or "rutoside" as used herein is refers to the glycoside combining the flavonol quercetin and the disaccharide rutinose ($\alpha$-L-rhamnopyranosyl-(1→6)-$\beta$-D-glucopyranose). It is a citrus flavonoid found in wide variety of plants including citrus fruit.

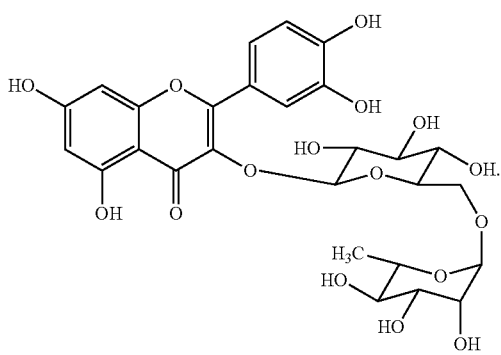 [SMILES: CC1OC(OCC2OC(Oc3c(-c4ccc(O)c(O)c4)oc4cc(O)cc(O)c4c3=O)C(O)C(O)C2O)C(O)C(O)C1O]

The term "methylsulfonylmethane" (MSM) as used herein refers to an organosulfur compound with the formula $(CH_3)_2SO_2$. MSM is also known by several other names including $DMSO_2$, methyl sulfone, and dimethyl sulfone. The structure of MSM is

The term "solubilization matrix" as used herein is meant to encompass a particular subset of solubilizers or a single solubilizer, in particular, wherein the solubilization matrix is selected from one or more of the following:
(i) chlorophyllin (CHL); (ii) green tea extract; (iii) epigallocatechin gallate (EGCG); (iv) Rutin; (v) or combinations of any of (i)-(iv).

The terms "solubilizer" as used herein refers to a substance that improves the solubility of a curcuminoid in water.

The term "solubility" as used herein refers to the property of a solid, liquid, or gaseous chemical substance ("solute") to dissolve in a solid, liquid, or gaseous solvent. The solubility of a substance fundamentally depends on the physical and chemical properties of the solute and solvent as well as on temperature, pressure and the pH of the solution.

The term "organic solvent" as used herein is refers to any solvent having at least 1 carbon atom and 1 hydrogen atom, a low molecular weight, lipophilicity, and volatility, and exist in liquid form at room temperature. Organic solvents may further be grouped as aliphatic or aromatic. Organic solvents are useful because they can dissolve oils, fats, resins, rubber, and plastics. An organic solvent may be selected from: methanol; ethanol; propanol; butanol; acetonitrile; and acetone.

Curcuminoids may be fully solubilized in chlorophyllin (CHL) at about 5% to about 70% by weight of a curcuminoid powder may be blended with a mixture of CHL and green tea extract or CHL alone. Alternatively, about 10% w/w to about 30% w/w of a curcuminoid powder may be blended with a mixture of CHL and green tea extract or CHL alone. A further alternative may include about 10% w/w to about 20% w/w of a curcuminoid powder is blended with a mixture of CHL and green tea extract or CHL alone. The content of CHL as a solubilizer may be from about 10% to about 95% by weight, or about 40% to about 80% by weight. The green tea extract used as a solubilizer may be from about 5% to about 90% by weight, or may be from about 20% to about 90% by weight, or may be from about 40% to about 90% by weight. The curcuminoid powder may be visually distinguishable in the chlorophyllin and green tea extract (if used) mixture as yellow particulates in the solution. However, when heat is applied (for example, until the solution reaches about 60-90° C. or at about 80° C.), the curcuminoid may become fully dissolved in chlorophyllin and green tea extract mixture as the particulates disappear and the solution turns to a transparent orange color. An organic solvent, or mixtures of solvents, including but not limited to methanol, ethanol, acetonitrile, acetone, propanol, and butanol may be added before or during the heating process and allowed to evaporate when heated. The solution of curcuminoid, chlorophyllin and green tea extract would then be allowed to cool to room temperature and return to solid form.

Solubility testing of the curcuminoid composition may proceeded as follows: 1 gram of curcuminoid composition added to 99 mL of water, and shaken vigorously in order to mix; then about 3 mL of solution is removed; then centrifuged at 6000*g for 5 minutes or, alternatively filtered through 0.2 μm filter; the top layer of the centrifuged solution or the filtrate may be used for HPLC analysis; and the filtrate after 0.2 μm filtration contains only water soluble curcumin particles smaller than 200 nm.

Curcuminoids are Fully Solubilized in Chlorophyllin (CHL)

About 5% to about 70% by weight of a curcuminoids powder was blended with a mixture of chlorophyllin and green tea extract. Alternatively, about 10% w/w to about 30% w/w of a curcuminoids powder was blended with a mixture of chlorophyllin and green tea extract. Alternatively, about 10% w/w to about 20% w/w of a curcuminoids powder was blended with a mixture of chlorophyllin and green tea extract. The content of chlorophyllin as a solubilizer may be from about 10% to 95% by weight, or most preferably from about 40% to about 80% by weight. The green tea extract used as a solubilizer may be from about 5% to about 90% by weight, or may be from about 20% to about 90% by weight, or may be from about 40% to about 90% by weight. At first, the curcuminoid powder is visually distinguishable in the chlorophyllin and green tea extract mixture as yellow particulates in the solution. However, when heat is applied to raise the solution temperature to about 60-90° C., or about 80° C., the curcuminoids become fully dissolved in chlorophyllin and green tea extract mixture as the particulates completely disappear and the solution turns to a transparent but orange color. An organic solvent, or mixtures of solvents, including but not limited to methanol, ethanol, acetonitrile, acetone, propanol, and butanol may be added before or during the heating process and allowed to evaporate during the process. The solution of curcuminoids, chlorophyllin and green tea extract is then allows to cool to room temperature and return to solid form.

Various alternative embodiments and examples are described herein. These embodiments and examples are illustrative and should not be construed as limiting the scope of the invention.

EXAMPLES

Example 1: Bioavailabilty of a Curcumin and Chlorophyllin (CHL) Composition

Seven volunteer subjects aged between 25 and 55 years of age as the test subject are selected. Initially, all of volunteers were advised to take a curcumin/CHL formula capsule as shown in TABLE 1 below. Blood samples were then collected before ingesting the capsules and then periodically at 1 hr up to 4 hrs. and then at 2 hr intervals for the remaining 4 hrs. until the end of 8 hours (see TABLE 2). After all blood samples were collected, the blood samples were processed as described below.

It is devised a method of manufacturing for novel curcumin-based composition. An exemplary method for producing a water-soluble curcumin having the properties is as follow:

(1) curcumin powder was dissolved in the same weight of ethanol, then mixed with CHL;

(2) dissolving and mixing in (1) was performed at a temperature of 80° C.; and (3) once dissolved, increase the temperature of the mixture above the boiling point of ethanol for a period 30-90 minutes to evaporate as much of the ethanol as much as possible.

TABLE 1

CURCUMIN AND CHL

| Ingredient | Input Amounts (g) | Input Ratios (% w/w) | Dried Wt (g) | Dried Ratios (% w/w) |
|---|---|---|---|---|
| Curcumin | 2 | 1.0 | 2 | 10.0 |
| Ethanol | 180 | 90.0 | 0 | 0 |
| CHL composition (Sodium copper) | 5.4 | 2.7 | 5.4 | 27.0 |
| Green tea extract | 12.6 | 6.3 | 12.6 | 63.0 |
| Total | 200 | 100.0 | 20 | 100.0 |

Example 2: Comparison Curcumin and CHL Composition to Commercial Products

Commercial curcumin products (reference #1—Theracurmin™ 30%. A commercial product made with micronized curcuminoids and gum ghatti, JP 2009-263638 A; reference #2—Longvide™ Curcumin. A commercial product with lipid micelles of curcuminoids and antioxidants) were compared against the curcuminoid/CHL composition set out in TABLE 1.

Figure 2:
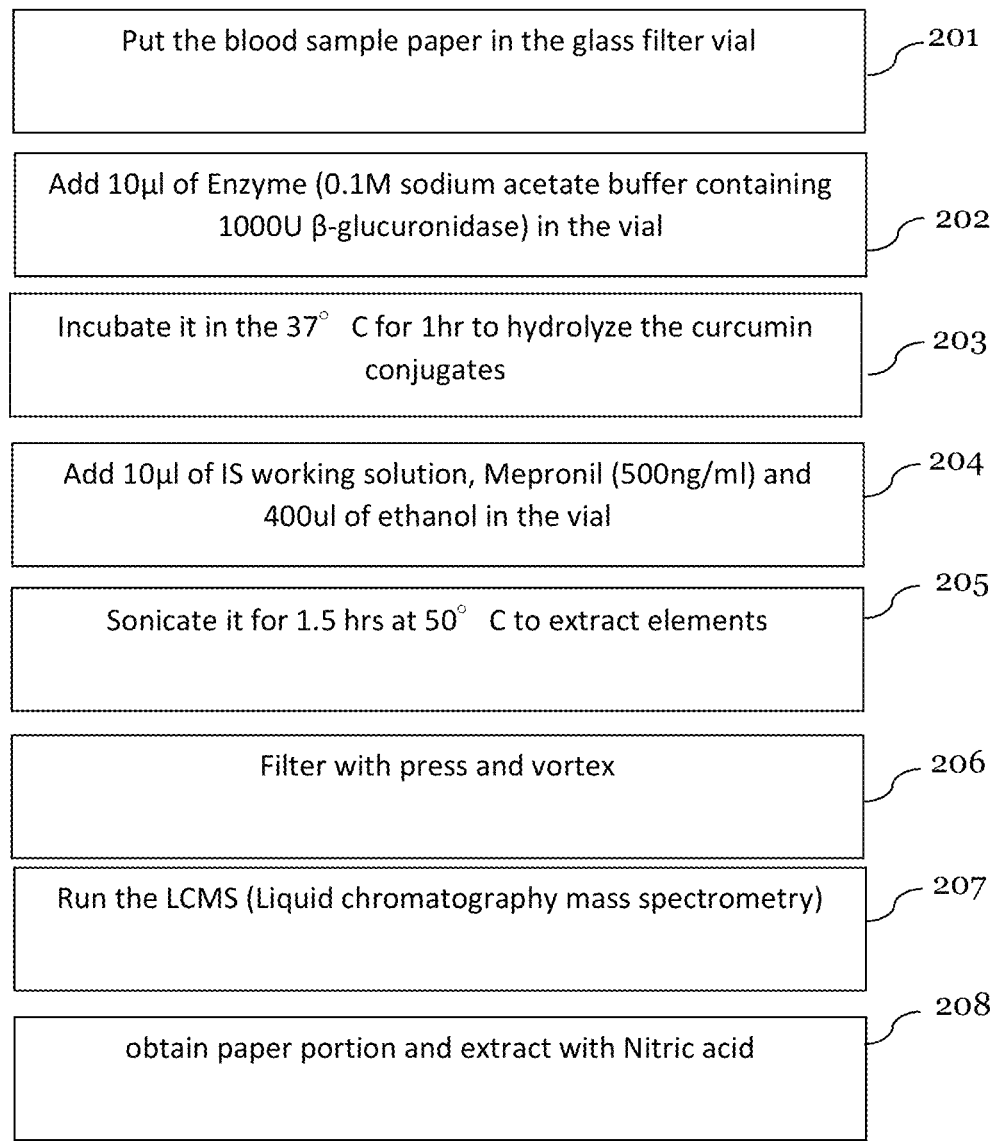
FIG. 2 shows a flow chart of extracting process for blood sample.

Seven volunteers aged between 25 and 55 years of age as the test subject were selected and first were advised to take a curcuminoid capsule reference #1 (Theracurmin™) or reference #2 (Longvide™ Curcumin). Blood samples were then collected before ingesting the capsules and then periodically at 1 hr up to 4 hrs. and then at 2 hr intervals for the remaining 4 hrs. until the end of 8 hours (see TABLE 2). After all blood samples were collected, the blood samples were processed as described FIG. 2.

TABLE 2

DATA COLLECTION TIME POINTS FOR TEST SUBJECTS 1-7

| Name Curcumin (mg) | V01 180 | V02 180 | V03 180 | V04 180 | V05 180 | V06 180 | V07 180 |
|---|---|---|---|---|---|---|---|
| 0 Hr | V1-0 | V2-0 | V3-0 | V4-0 | V5-0 | V6-0 | V7-0 |
| 1 Hr | V1-1 | V2-1 | V3-1 | V4-1 | V5-1 | V6-1 | V7-1 |
| 2 Hr | V1-2 | V2-2 | V3-2 | V4-2 | V5-2 | V6-2 | V7-2 |
| 3 Hr | V1-3 | V2-3 | V3-3 | V4-3 | V5-3 | V6-3 | V7-3 |
| 4 Hr | V1-4 | V2-4 | V3-4 | V4-4 | V5-4 | V6-4 | V7-4 |

TABLE 2-continued

DATA COLLECTION TIME POINTS FOR TEST SUBJECTS 1-7

| Name Curcumin (mg) | V01 180 | V02 180 | V03 180 | V04 180 | V05 180 | V06 180 | V07 180 |
|---|---|---|---|---|---|---|---|
| 6 Hr | V1-6 | V2-6 | V3-6 | V4-6 | V5-6 | V6-6 | V7-6 |
| 8 Hr | V1-8 | V2-8 | V3-8 | V4-8 | V5-8 | V6-8 | V7-8 |

*V01-07 refers to each of the seven (7) volunteer test subjects.

Figure 3A:
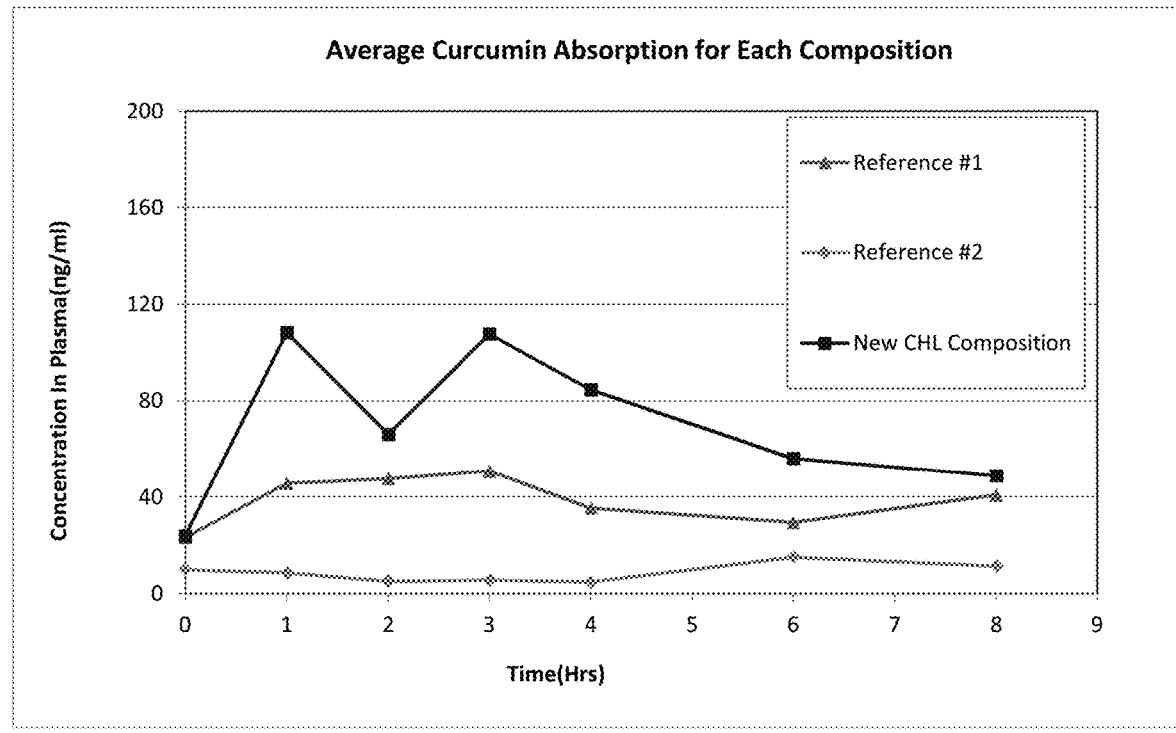
FIG. 3A shows a graph comparing curcumin absorption overtime for a CHL composition and two reference compositions.
Figure 3B:
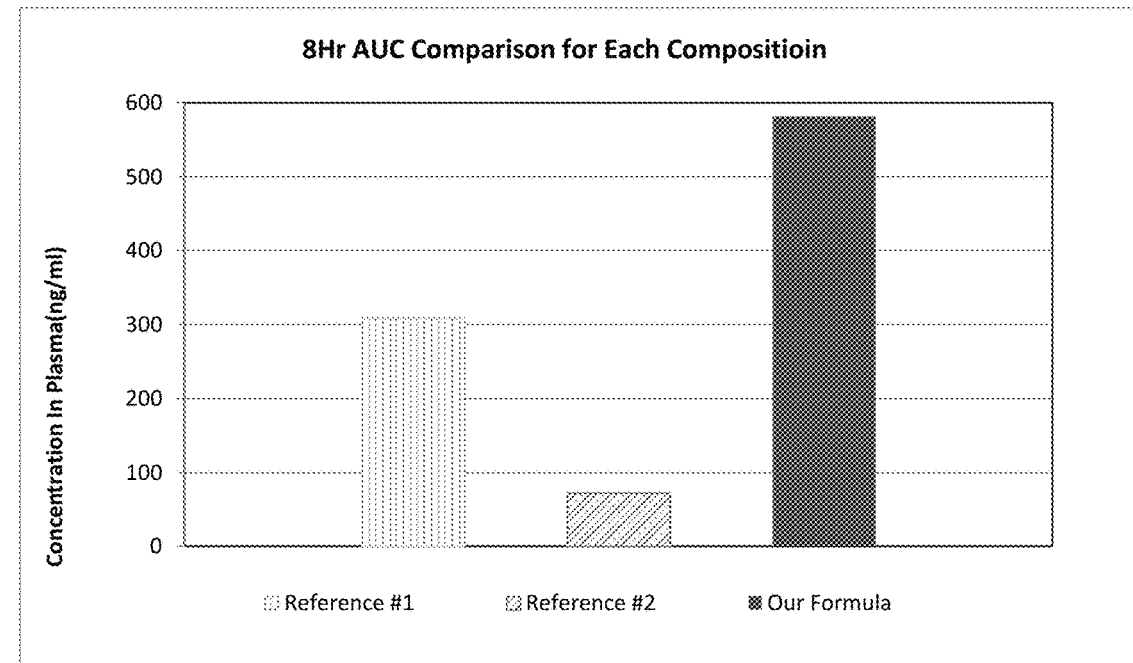
FIG. 3B shows a graph comparing total area under the curve (AUC) curcumin absorption for a CHL composition and two reference compositions.

Existing commercial curcumin products (Reference #1 and #2 as described above) were compared against a curcumin and CHL composition using the same procedure with a wash out period of at least one week. The curcuminoid and CHL composition (TABLE 1) showed higher total plasma concentrations of curcumin than commercial curcumin products (see FIG. 3B) and showed higher plasma concentrations over a longer time course than commercial curcumin products (see FIG. 3A). The CHL water-soluble curcumin composition shows superior performance compared to other commercial compositions. The results described herein show that the curcuminoid CHL composition provides an improvement of at least 88% compared to other commercially available compositions.

Figure 4A:
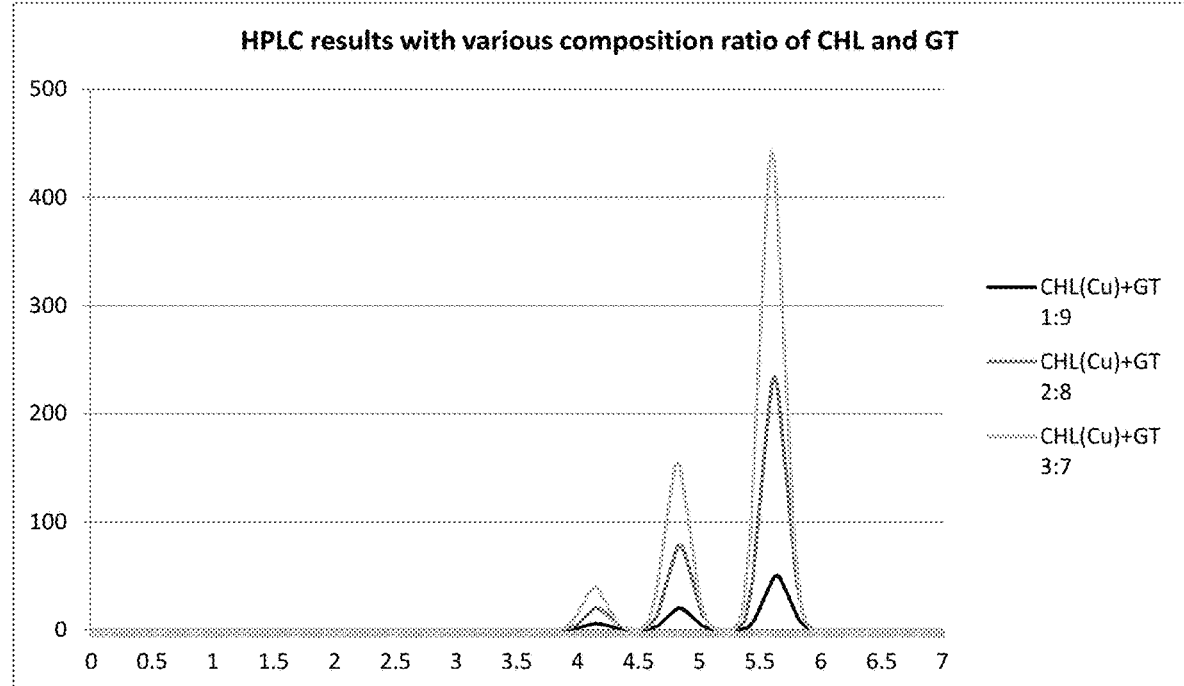
FIG. 4A shows a plot comparing HPLC results for curcumin and compositions of CHL with GT.
Figure 4B:
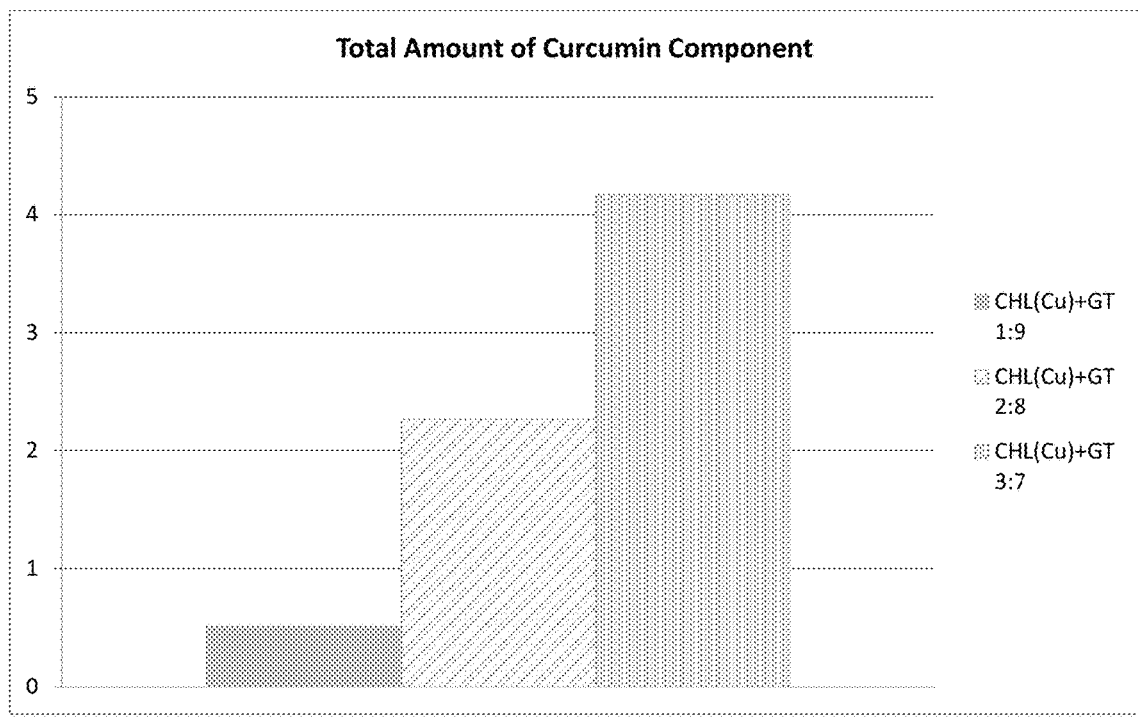
FIG. 4B shows a graph of total amount of curcumin component for curcumin and composition of CHL with GT by HPLC analysis.
Figure 5A:
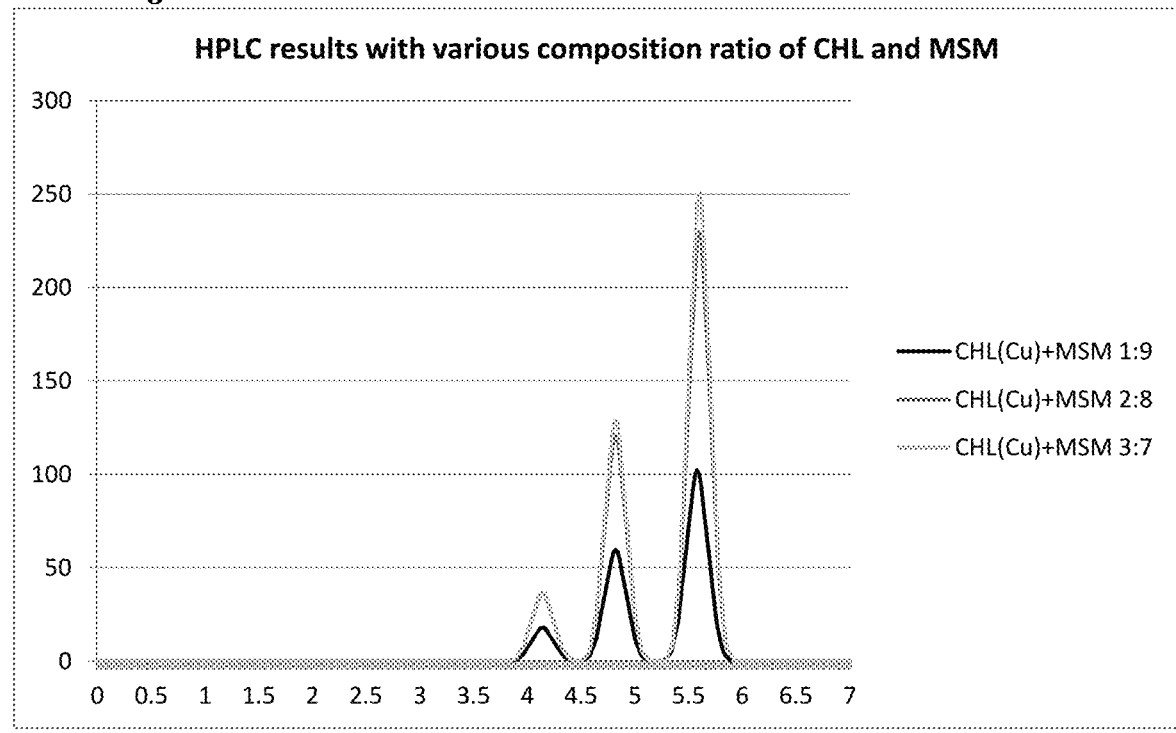
FIG. 5A shows a plot comparing HPLC results for curcumin and compositions of CHL with MSM.
Figure 5B:
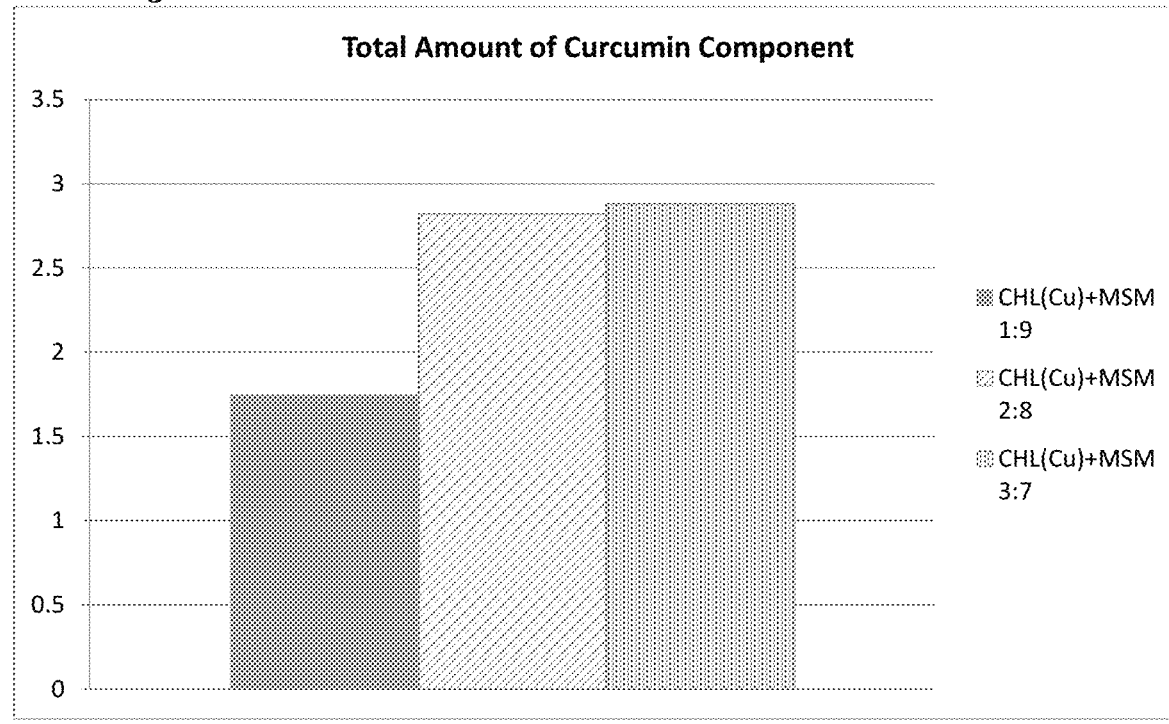
FIG. 5B shows a graph of total amount of curcumin component for curcumin and composition of CHL with MSM by HPLC analysis.
Figure 6A:
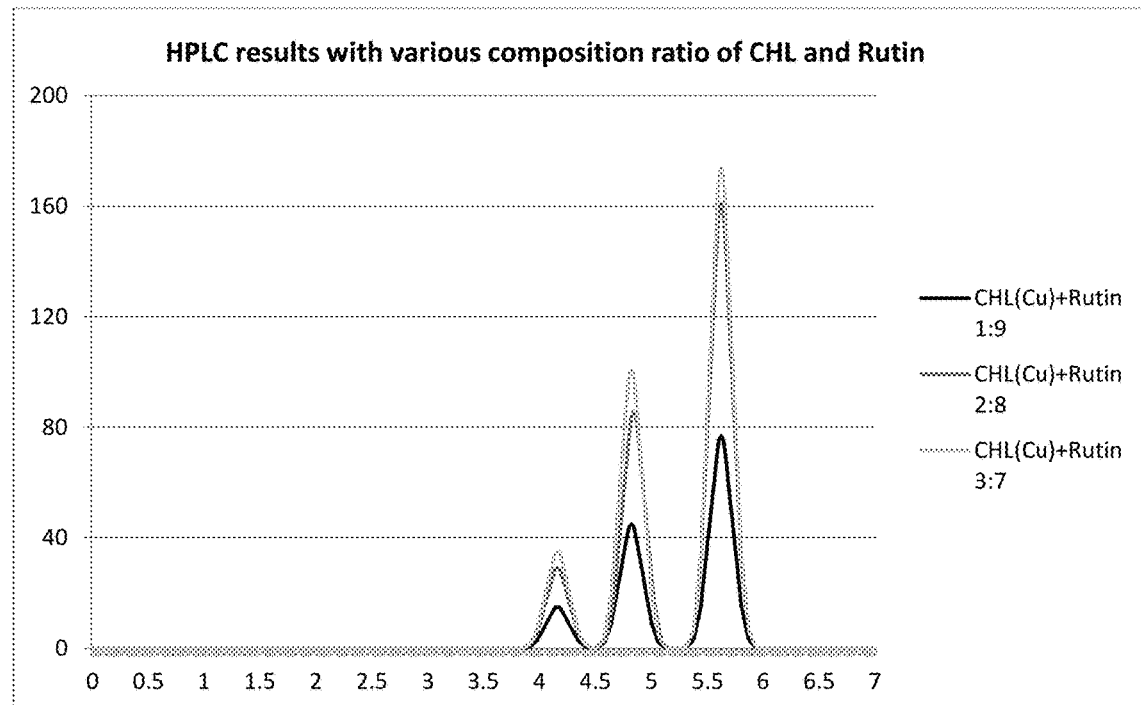
FIG. 6A shows a plot comparing HPLC results for curcumin and compositions of CHL with Rutin.
Figure 6B:
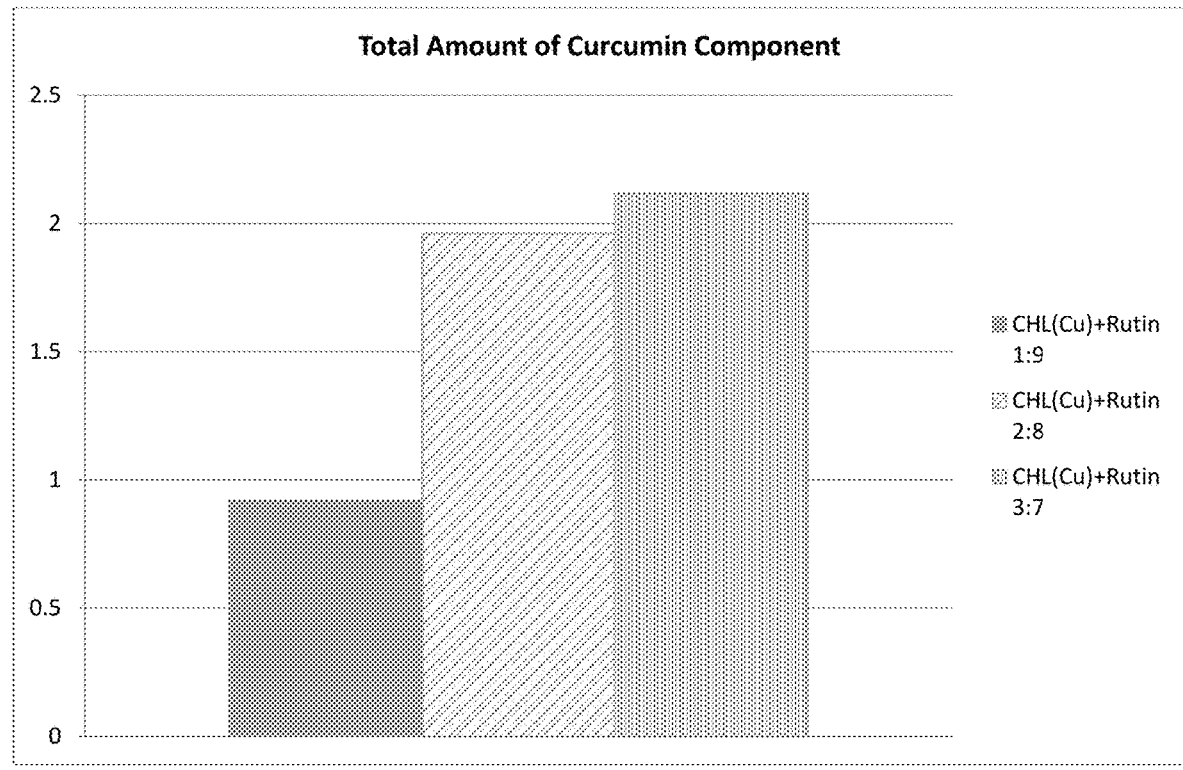
FIG. 6B shows a graph of total amount of curcumin component for curcumin and composition of CHL with Rutin by HPLC analysis.

Example 3: High Performance Liquid Chromatography (HPLC) Analysis of CHL Compositions with Three Alternative Solubilizers Human subjects were administered composition prepared comprising (1) curcuminoid and chlorophyllin (CHL) with green tea extract (GT); (2) curcuminoid and chlorophyllin (CHL) with methylsulfonylmethane (MSM); and (3) curcuminoid and chlorophyllin (CHL) with Rutin. Furthermore, HPLC was used to compare three ratios of CHL to the second solubilizer (i.e. GT, MSM or Rutin (i.e. ratios of either 1:9, 2:8 and 3:7). Blood sampling and extraction was conducted as set out in FIG. 2, prior to HPLC (High Performance Liquid Chromatography) analysis of the extract. As shown in FIG. 4A and FIG. 4B, CHL with GT was compared at three ratios (i.e. 1:9, 2:8 and 3:7). The highest concentrations of curcuminoid was found in compositions having higher CHL relative to GT (i.e. 3:7 ratio). Similarly, as shown in FIG. 5A and FIG. 5B, CHL with MSM was compared at three ratios (i.e. 1:9, 2:8 and 3:7). Although the total curcuminoid concentration was lower than in for CHL with GT, there was still a trend towards increased concentrations of curcuminoid in compositions having higher CHL relative to MSM (i.e. 2:8 and 3:7 ratio). Similar to the CHL with MSM, as shown in FIG. 6A and FIG. 6B, CHL with Rutin was compared at three ratios (i.e. 1:9, 2:8 and 3:7). Although the total curcuminoid concentration was lower than in for CHL with GT and CHL with MSM, there was still a trend towards increased concentrations of curcuminoid in compositions having higher CHL relative to Rutin (i.e. 2:8 and 3:7 ratio).

The use of CHL increases the amount of curcuminoid component present in the blood and plasma when compared to other commercially available curcumin products. Accordingly, the use of CHL has positive role the delivery of curcuminoids.

The optimal ratio of CHL and GT for maximum absorption of curcumin is 3:7. Compared with other ratios tested, the composition with 3:7 ratio shows about 8 times the amount of curcumin.

TABLE 3

Water Solubilities of Various Curcuminoid Compositions

| Description | Water (g) | MSM (g) | TYR (g) | Green Tea extract (g) | TRP (g) | PHE (g) | CHL-Mg (g) | Curcumin (g) | Water Solubility or Curcumin Solubility in Water (%, HPLC) |
|---|---|---|---|---|---|---|---|---|---|
| MSM only (10% Curcumin) | 8.1 | 0.9 | | | | | | 0.1 | Grade 1 |
| MSM + Green tea Ext (10% Curcumin) | 7.2 | 0.9 | | 0.9 | | | | 0.2 | Grade 3 |
| *CHL(Mg) + Tyrosine(3:7) | | | 0.63 | | | | 0.27 | 0.1 | 1.21 |
| *CHL(Mg) + Tyrosine(4:6) | | | 0.54 | | | | 0.36 | 0.1 | 2.27 |
| *CHL(Mg) + Tyrosine(5:5) | | | 0.45 | | | | 0.45 | 0.1 | 3.25 |
| *CHL(Mg) + Green tea(3:7) | | | | 0.63 | | | 0.27 | 0.1 | 3.8 |
| *CHL(Mg) + Green tea(4:6) | | | | 0.54 | | | 0.36 | 0.1 | 3.69 |
| *CHL(Mg) + Green tea(5:5) | | | | 0.45 | | | 0.45 | 0.1 | 4.3 |
| *CHL(Mg) + Tryptophan(7:3) | | | | | 0.27 | | 0.63 | 0.1 | 1.31 |
| *CHL(Mg) + Tryptophan(6:4) | | | | | 0.36 | | 0.54 | 0.1 | 1.66 |
| *CHL(Mg) + Tryptophan(5:5) | | | | | 0.45 | | 0.45 | 0.1 | 1.09 |
| *CHL(Mg) + Phenylalanine(7:3) | | | | | | 0.27 | 0.63 | 0.1 | 1.53 |
| *CHL(Mg) + Phenylalanine(6:4) | | | | | | 0.36 | 0.54 | 0.1 | 1.66 |
| *CHL(Mg) + Phenylalanine(5:5) | | | | | | 0.45 | 0.45 | 0.1 | 1.54 |

*EtOH suspension

The optimal ratio of CHL and MSM for maximum absorption of curcumin is 3:7. Compared with other ratio of composition, the composition with 3:7 ratio shows about 1.7 times the amount of curcumin.

The optimal ratio of CHL and Rutin for maximum absorption of curcumin is 3:7. Compared with other ratio of composition, the composition with 3:7 ratio shows about 2.3 times the amount of curcumin.

Example 4: Analytical Method for Determining Curcumin in Blood

The present application also discloses an analytical method for determining curcumin in a subject's plasma sample (see FIG. 1) as set out below:

1. 0.05 mL aliquot of each plasma sample collected from rats and human subjects is transferred to a 2 mL glass tube.
2. 0.11 mL of 0.1M sodium acetate buffer (pH 5.0) containing 0.01 mL 3-glucuronidase is added.
3. The resulting solutions (2) are incubated to hydrolyze the curcumin conjugated at 37 degree Celsius for 1 hr.
4. 0.01 mL of mepronil working solution (20 ng/mL in 50% MeOH) is added.
5. 0.5 mL of chloroform as an extraction solvent is added.
6. The sample is vortexed for 1 min, followed by ultrasonic vibrations for 15 min and then centrifugation at 13000*g for 5 min.
7. The organic layer is transferred to a new 1 mL glass tube and evaporated to dryness using a centrifuge concentrator.
8. The treatment (5-7) is repeated once again. (add the organic layer to the same tube)
9. The dried extract is reconstituted in 0.1 mL of 50% MeOH and then centrifuged at 13000*g for 5 min.
10. 0.002 mL aliquot of supernatant of reconstituted sample solution is injected into a chromatographic system.

Although various embodiments are described herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as any open-ended term, substantially equivalent to the phrase "including, but not limited to", and the words "comprise" and "comprises" have a corresponding meaning. As used herein, the singular forms "a", "an" and "the" include plural referents unless the context clearly dictates otherwise. Thus, for example, reference to "a thing" includes more than one such thing. The invention includes all embodiments and variations substantially as hereinbefore described and with reference to the examples and drawings.

Citation of references herein is not an admission that such references are prior art nor does it constitute any admission as to the contents or date of these documents.

What is claimed is:

1. A solid composition, comprising:
   (a) a curcuminoid;
   (b) a first solubilizer comprising chlorophyllin (CHL); and
   (c) a second solubilizer comprising methylsulfonylmethane (MSM);

wherein the ratio of the first solubilizer to the second solubilizer is from 2:8 to 3:7, wherein the composition is made by the process, comprising:

mixing the curcuminoid and a solubilization matrix including at least the chlorophyllin (CHL), the methylsulfonylmethane (MSM), and a C1 to C4 alcohol to form a mixture;

adjusting the temperature of the mixture to dissolve the curcuminoid;

removing the C1 to C4 alcohol through evaporation; and cooling the mixture to permit the curcuminoid and the solubilization matrix composition to achieve a solid form.

2. The composition of claim 1, wherein the curcuminoid is between 10-30% w/w and the first and second solubilizers are between 70-90% w/w.

3. The composition of claim 1, wherein the weight percentage of curcuminoid is between about 5% and about 70%.

4. The composition of claim 1, wherein the weight percentage of first and second solubilizers is between about 10% and about 50%.

5. A solid composition, comprising:
(a) a curcuminoid, wherein the curcuminoid is between 10-30% w/w;
(b) a first solubilizer comprising chlorophyllin (CHL); and
(c) a second solubilizer comprising methylsulfonylmethane (MSM);

wherein the ratio of the first solubilizer to the second solubilizer is from 2:8 to 3:7, and wherein the first and second solubilizers are between 70-90% w/w, wherein the composition is made by the process, comprising:

mixing the curcuminoid and a solubilization matrix including at least the chlorophyllin (CHL), the methylsulfonylmethane (MSM), and a C1 to C4 alcohol to form a mixture;

adjusting the temperature of the mixture to dissolve the curcuminoid;

removing the C1 to C4 alcohol through evaporation; and cooling the mixture to permit the curcuminoid and the solubilization matrix composition to achieve a solid form.

6. The composition of claim 5, wherein the composition is encapsulated.

7. The composition of claim 5, wherein the composition is encapsulated with pharmaceutically acceptable lubricants and fillers.

8. The composition of claim 1, wherein the weight percentage of curcuminoid is between about 10% and about 50%.

* * * * *